United States Patent [19]

Cavazza

[11] Patent Number: 4,892,729

[45] Date of Patent: Jan. 9, 1990

[54] SOAP-FREE, BRUSHLESS NON-LATHERING SHAVING CREAM

[75] Inventor: Paolo Cavazza, Rome, Italy

[73] Assignee: Avantgarde S.p.A., Pomezia, Italy

[21] Appl. No.: 166,317

[22] Filed: Mar. 10, 1988

[30] Foreign Application Priority Data

Mar. 18, 1987 [IT] Italy .................................. 47739 A/87

[51] Int. Cl.$^4$ ................................................ A01K 7/15
[52] U.S. Cl. ...................................... 424/73; 514/772; 514/789
[58] Field of Search ................... 424/73; 514/772, 788, 514/789, 939, 941, 942, 975

[56] References Cited

U.S. PATENT DOCUMENTS 2,085,733 7/1937 Bird ........................................ 424/73
3,341,418 9/1967 Moses et al. .......................... 424/73

*Primary Examiner*—Ellis P. Robinson
*Assistant Examiner*—Susan S. Rucker
*Attorney, Agent, or Firm*—Ladas & Parry

[57] ABSTRACT

A soap-free, brushless non-lathering shaving cream is disclosed, which is endowed with both a potent softening action on the beard hair and emollient and curative action on the skin, characterized in that it comprises, instead of stearic acid and its sodium and triethanolamine salts that are generally used in conventional shaving cream formulations, from 4 to 15% by weight of a long-chain alcohol selected from stearyl, lauryl, cetyl, myristyl alcohol and mixtures thereof.

10 Claims, No Drawings

SOAP-FREE, BRUSHLESS NON-LATHERING SHAVING CREAM

DESCRIPTION

The present invention relates to a soap-free, brushless non-lathering shaving cream, that is endowed with potent softening action on the beard hair and emollient and curative action on the skin which is lubricated and conditioned by the cream so as to make it suitably ready for shaving.

Although brushless non-lathering shaving creams are not yet widely marketed, they present several advantages over both aerosol shaving foams and lather shaving soaps which require a brush for forming the foam and lathering the face.

These advantages are:

(1) less irritation to the skin, particularly delicate and broken skin, owing to the slightly basic pH (7.5-8.5) that is lower than the far higher pH (pH=10) of lather shaving creams;

(2) the emollient and protective effect to the skin that reduces razor drag, owing to the thick film of lubricant on the face.

The known non-lathering shaving creams possess, however, several disadvantages which are likely to be the cause for less popularity among consumers than conventional foamed shaving preparations, and hence their more limited spread on the market.

Mainly, these disadvantages are:

(i) excess of cream and shaving debris are difficult to rinse from the razor with attendant less effectiveness of the razor in subsequent shavings;

(ii) brushless creams can leave the skin feeling greasy; or on the contrary (iii) a too rapid absorption might adversely affect the comfort and closeness of the shave;

(iv) less effectiveness than lather-forming preparations in the hair-softening action with attendant more rapid dulling of the blade edge; and (v) brushless cream pH cannot be lower than 7.5-8.

The known brushless non-lathering shaving creams are oil-in-water emulsions whose compositions are similar to those of vanishing creams, the main difference being that the concentration of oils and emulsifying agents is higher in shaving preparations.

Typically, the oil phase of known brushless preparations comprises: 4–10% of lubricant (e.g. mineral oils, long-chain fatty acid esters, VASELINE); 10–25% of stearic acid as superfatting agent and to provide the characteristic pearlescent appearance of the shaving cream; 1–4% of emollient such as spermaceti, cetyl alcohol, stearyl alcohol and lanolin. Spermaceti is preferably utilized as a means for preventing the cream from vanishing too rapidly, i.e. before shaving is completed. VASELINE (petrolatum) is a purified mixture of semi-solid hydrocarbons, chiefly of the methane series of the general formula $C_nH_{2n+2}$.

The aqueous phase usually contains: 1–5% of soaps such as potassium and triethanolamine stearate; 0–5% of synthetic surfactants to increase emulsion stability, beard hair wetting and to facilitate skin rinsibility such as glycerol monostearate and fatty acid amides; 0–1% of thickening agents such as gum tragacanth, sodium alginate, polyvinylpyrrolidone, polyacrylic acid; and 2–10% of humectant agents to prevent drying-out of the shaving cream such as glycerol, sorbitol and propylene glycol. Usually, preservatives, perfumes, bacteriostats and other additives are included.

The main disadvantages that are the rapid dulling of the blade edge and the difficulty to rinse the remaining cream from the razor blade are to be attributed to stearic acid in the compositions.

The brushless non-lathering shaving cream of the present invention does not present the above-identified shortcomings.

In particular, the brushless non-lathering shaving cream of the present invention is endowed with a potent softening action on the beard hair, it can be easily rinsed from the razor, it does not dull the blade edge and it does not make the skin feeling greasy. On the contrary, following regular use of the cream, the skin rapidly becomes soft and elastic.

Moreover, the brushless non-lathering shaving cream of the present invention does not provoke irritation to the skin brought about by the soap and allows the use of the after-shave lotions to be eliminated. Finally, the cream pH can be adjusted to the slight acidic pH of the skin.

The non-lathering shaving cream of the present invention is characterized in that it comprises the following components:

(a) from 4 to 15% by weight of a long-chain alcohol selected from stearyl alcohol, lauryl alcohol, cetyl alcohol, myristyl alcohol and mixtures thereof;

(b) from 1 to 10% by weight of an anionic, nonionic, amphoteric or quaternary surfactant and/or emulsifying agent, provided that if the quaternary surfactant is present the anionic surfactant is absent;

(c) from 1 to 10% by weight of a wetting agent selected from glycerol, propylene glycol, sorbitol and polyethylene glycol; and (d) from 4 to 20% by weight of an emollient selected from mineral oils and vaseline.

It will be noted that the shaving cream of the invention is totally free of both stearic acid and soaps. The shortcomings brought about by stearic acid have been previously illustrated. Lack of soap allows quaternary surfactants that exhibit preservative and detergent action to be incorporated into the shaving cream. A further advantage derives from the possibility of adding hypoallergenic surfactants to the shaving cream of this invention and adjusting its pH within wide ranges. For instance, it will be possible to adjust its pH to the slight acidic value of the skin (5.5–6.5).

Alcohol (a) gives consistency and texture to the cream and acts as superfatting agent. Alcohol (a) percentage will be suitably comprised between 4 and 12% by weight and is preferably about 8% by weight. More than about 12% would make the shaving uncomfortable and the cream would be less easy to rinse from the razor. Less than 4% would bring about excessive cream fluidity and less cream protection to the skin because of too direct friction between the razor blade and skin.

The anionic surfactants will be preferably selected from: isethionates, acylglutamates, sarcosinates (e.g. sodium cocoyl isethionate, sodium cocoyl glutamate, sodium cocoyl sarcosinate), laurylsulfate, laurylethersulfate with 2-3-4 and more ethylene oxide moles, semisulfosuccinates (e.g. ricinoleylmonoethanolamide bisodium semisulfoccinate), cetylstearyl alcohol with about 12 ethylene oxide moles (EMULGIN B1), 20 ethylene oxide moles (EMULGIN B2), 30 ethylene oxide moles (EMULGIN B3).

The nonionic surfactants will be preferably selected from: ethoxylated and propoxylated alcohols, the TWEEN series (TWEEN 20-40-60-80), (TWEEN 20, TWEEN 40, TWEEN 60 AND TWEEN 80 correspond to the compounds of polysorbate 20, 40, 60 and 80 respectively), the SPAN series (SPAN 20-40-60-80). According to the CTFA cosmetic Ingredient Dictionary, SPAN 20 is sorbitan laurate, SPAN 40 is sorbitan palmitate, SPAN 60 is sorbitan stearate, and SPAN 80 is sorbitan oleate.), amides of fatty acids such as cocoyl monoethanolamide, cocoyl diethanolamide, cocoyl isopropylamide.

The amphoteric surfactants will be preferably selected from: alkylamidobetaine (e.g. (cocoyl amidopropylbetaine inner salt), alkylbetaine (e.g. laurylbetaine inner salt), imidazoline.

The quaternary surfactants will be preferably selected from: isostearamidopropyl ethyldiammoniumethosulfate, isostearylethyl imidoniumethosulfate, alkyldimethylbenzyl-ammonium saccharate, hydroxyethylcellulose trimethylammonium chloride, cetylpyridinium chloride.

The noionic and amphoteric surfactants are preferred to anionic surfactants because they are more compatible to the skin and because they can be used in association with quaternary surfactants (these would not be compatible in association with anionic surfactants) which have a preservative action on the cream and an antiseptical action on the skin.

The quaternary ammonium surfactants exhibit antistatic action by scattering the electrostatic charges of keratin fibers which accumulate because of the razor drag over the skin.

The following non limiting examples illustrate some soap-free non-lathering shaving cream formulations (% by weight) in accordance with the present invention.

| FORMULATION | 1 | 2 | 3 | 4 | 5 | 6 |
|---|---|---|---|---|---|---|
| Solid petrolatum | 1 | — | 1 | 2 | — | 1 |
| EMULGIN B1 | 2.2 | 2.2 | 2 | — | — | — |
| TWEEN 60 | 1 | 1 | 2 | 2 | 2 | 1 |
| Liquid petrolatum | 11 | 11 | 11 | 11 | 10 | 11 |
| Cetylstearyl alcohol | 6 | 8 | 7.5 | 5 | 7 | 6 |
| Silicone oil | 1 | 1 | 2 | 2 | 2 | 2 |
| Sorbitol | 7 | — | — | — | — | — |
| Glycerol | — | 7 | — | 7 | 7 | 7 |
| Propyleneglycol | — | — | 7 | — | — | — |
| Antioxidant | q.s. | q.s. | q.s. | q.s. | q.s. | q.s. |
| Perfume | q.s. | q.s. | q.s. | q.s. | q.s. | q.s. |
| Preservative | q.s. | q.s. | q.s. | q.s. | q.s. | q.s. |
| Tego Betaine | — | — | — | — | — | 4 |
| STEINOQUAT Q.A. 100 | — | — | — | — | — | 0.2 |
| Lauryl sulfate | — | — | — | 1 | — | — |
| Sodium isethionate | — | — | — | — | 1 | — |
| PVP | 1 | — | 1 | — | — | — |
| Stearic Acid | — | — | — | — | — | 2 |
| Water, balance to | 100 | 100 | 100 | 100 | 100 | 100 | q.s. (quantum sufficit) = as much as suffices

The various components are compounded according to procedures well known to the experts in shaving cream technology.

What is claimed is:

1. A brushless non-lathering shaving cream characterized in that it comprises the following components:
    (a) from 4 to 15% by weight of a long-chain alcohol selected from stearyl alcohol, lauryl alcohol, cetyl alcohol, myristyl alcohol and mixtures thereof;
    (b) from 1 to 10% by weight of an anionic, nonionic, amphoteric or quaternary surfactant and emulsifying agent, provided that if the quaternary surfactant is present the anionic surfactant is absent, or
    (c) from 1 to 10% by weight of an anionic, nonionic, amphoteric or quaternary surfactant or emulsifying agent, provided that if the quaternary surfactant is present the anionic surfactant is absent;
    (d) from 1 to 10% by weight of a wetting agent selected from glycerol, propylene glycol, sorbitol and polyethylene glycol; and
    (e) from 4 to 20% by weight of an emollient selected from mineral oils and VASELINE (petrolatum).

2. The shaving cream of claim 1 characterized in that the anionic surfactants are preferably selected from: isethionates, acylglutamates, sarcosinates, laurylsulfate, laurylethersulfate with 2-3-4 and more ethylene oxide moles, semisulfosuccinates, cetylstearyl alcohol with about 12 ethylene oxide moles (EMULGIN B1), 20 ethylene oxide moles (EMULGIN B2), and 30 ethylene oxide moles (EMULGIN B3).

3. The shaving cream of claim 1 characterized in that the nonionic surfactants are preferably selected from: ethoxylated and propoxylated alcohols, the TWEEN series (TWEEN 20-40-60-80), the SPAN series (SPAN 20-40-60-80), and amides of fatty acids.

4. The shaving cream of claim 1 characterized in that the amphoteric surfactants are preferably selected from: alkylamidobetaine, alkylbetaine, and imidazoline.

5. The shaving cream of claim 1 characterized in that the quaternary surfactants are preferably selected from: isostearamidopropyl ethyldiammoniumethosulfate, isostearylethyl imidoniumethosulfate, alkyldimethylbenzylammonium saccharate, hydroxyethylcellulose trimethylammonium chloride, cetylpyridinium chloride.

6. The shaving cream of claim 2 wherein the sarcosinates are selected from the group consisting of sodium cocoyl isethionate, sodium cocoyl glutamate and sodium cocoyl sarcosinate.

7. The shaving cream of claim 2 wherein the semisulfosuccinate is ricinoleylmonoethanolamide bisodium semisulfosuccinate.

8. The shaving cream of claim 3 wherein the amides of fatty acids are selected from the group consisting of cocoyl monoethanolamide, cocoyl diethanolamide and cocoyl isopropylamide.

9. The shaving cream of claim 4 wherein the alkylamidobetaine is cocoylamidopropylbetaine inner salt.

10. The shaving cream of claim 4 wherein the alkylbetaine is laurylbetaine inner salt.

* * * * *